United States Patent [19]

Fincke et al.

[11] Patent Number: 5,470,343
[45] Date of Patent: Nov. 28, 1995

[54] DETACHABLE POWER SUPPLY FOR SUPPLYING EXTERNAL POWER TO A PORTABLE DEFIBRILLATOR

[75] Inventors: Randall W. Fincke, Winchester; Michael L. Lopin, Newton; Frederick W. Faller, Burlington, all of Mass.

[73] Assignee: ZMD Corporation, Wilmington, Del.

[21] Appl. No.: 258,238

[22] Filed: Jun. 10, 1994

[51] Int. Cl.[6] .................................................. A61N 1/39
[52] U.S. Cl. ............................. 607/5; 439/341; 439/909
[58] Field of Search ............................. 607/5–8; 439/338, 439/341, 909

[56] References Cited

U.S. PATENT DOCUMENTS

| | | | |
|---|---|---|---|
| 3,728,664 | 4/1973 | Hurst | 439/341 |
| 3,758,839 | 9/1973 | Medlar | 320/32 |
| 3,862,636 | 1/1975 | Bell et al. | 128/419 D |
| 3,865,101 | 2/1975 | Saper et al. | 128/2.06 R |
| 3,969,796 | 7/1976 | Hodsdon et al. | 439/341 |
| 4,019,111 | 4/1977 | Bennefeld | 320/23 |
| 4,077,413 | 3/1978 | Partridge | 128/419 D |
| 4,080,558 | 3/1978 | Sullivan | 320/39 |
| 4,119,903 | 10/1978 | Pirkle | 320/1 |
| 4,233,659 | 11/1980 | Pirkle | 363/134 |
| 4,639,656 | 1/1987 | Mukai | 320/22 |
| 4,952,861 | 8/1990 | Horn | 320/23 |
| 5,014,697 | 5/1991 | Pless et al. | 607/7 |
| 5,088,489 | 2/1992 | Lerman | 128/419 |
| 5,089,763 | 2/1992 | Van Der Linden et al. | 320/20 |
| 5,163,428 | 11/1992 | Pless | 128/419 D |
| 5,224,870 | 7/1993 | Weaver et al. | 607/5 |
| 5,233,659 | 8/1993 | Ahlberg | 381/30 |
| 5,237,259 | 8/1993 | Sanpei | 320/23 |
| 5,243,975 | 9/1993 | Alferness et al. | 607/7 |

FOREIGN PATENT DOCUMENTS

| | | | |
|---|---|---|---|
| 1496982 | 1/1978 | United Kingdom | 607/5 |

*Primary Examiner*—William E. Kamm
*Attorney, Agent, or Firm*—Fish & Richardson

[57] ABSTRACT

A detachable power supply for supplying power from an external power source to a portable defibrillator for charging a battery of the portable defibrillator and operating the portable defibrillator includes a housing shaped to attach to the portable defibrillator and a latch connected to the housing for mechanically attaching the power supply to the defibrillator so that the power supply and the defibrillator form a portable, integral unit. The power supply also includes an electrical connector connected to the housing to supply power from the power supply to the defibrillator, the connector is located so that it engages a mating electrical connector on the defibrillator as the latch is engaged to connect the power supply to the defibrillator, an external power connection for bringing external power into the power supply, and a power module installed within the housing, the power module having a power circuit that converts power from the external power source to a form useable by the defibrillator, the output of the power module being connected to the electrical connector to deliver power to the defibrillator. Typically, the power module is alternately operable in both a controlled current mode and a controlled voltage mode.

34 Claims, 6 Drawing Sheets

DETACHABLE POWER SUPPLY FOR SUPPLYING EXTERNAL POWER TO A PORTABLE DEFIBRILLATOR

BACKGROUND OF THE INVENTION

The invention relates to power supplies and battery chargers for portable defibrillators.

Portable defibrillators, such as the PD 1400 Series Products available from Zoll Medical Corporation of Burlington, Mass., deliver high energy shocks to a patient's chest for defibrillation. Typically, portable defibrillators employ batteries (e.g., lead acid batteries) to store power for generating such shocks. Eventually, the power stored in the batteries is used, and the batteries must be recharged from a source of AC power.

AC power supplies, which convert AC power to DC power, have been used for operating a portable defibrillator and for recharging the batteries in the portable defibrillator. Approaches to using AC power supplies include: building an AC power supply into the portable defibrillator; supplying an AC power supply in a separate box that includes a cord for attachment to the portable defibrillator; attaching the portable defibrillator into a "docking station" that contains an AC power supply (so that the combination of the docking station and the portable defibrillator is not itself portable); and removing the batteries from the portable defibrillator for charging in a separate AC powered unit (in which case the AC powered unit does not power the defibrillator). The conventional AC power supply is a "controlled voltage" supply that maintains a controlled, generally constant, DC output voltage for varying electrical load.

Controlled current supplies, which maintain a controlled, generally constant, DC output current for varying electrical load, have been used in other types of devices in which batteries need to be charged. Controlled current supplies offer advantages over controlled voltage supplies in that controlled current supplies can more rapidly charge batteries and can provide a more reliable indication that a battery is fully charged. Controlled current supplies are particularly well suited to charging lead acid and other types of batteries that tend to lose the ability to retain a charge when put into use before being fully charged. When such batteries are charged with a controlled voltage supply, the user sometimes will think that the battery is fully charged, both because charging takes so long (e.g., sixteen hours) and because the charger cannot reliably inform the user whether charging is complete, with the result that partially charged batteries are inadvertently put into use. Over time, use of partially charged batteries results in the batteries losing their ability to retain a charge. Though providing superior charging characteristics with regard to the time required to charge a battery, previous controlled current chargers have required complex support circuitry to implement them as AC power supplies for defibrillators. The difficulty with implementing controlled current chargers is that they must maintain a measure of the current supplied to the battery, and therefore, without support circuitry, require a known charging current into the battery to perform properly. When a defibrillator is operating, however, current levels may vary from as low as 500 milliamps up to eight amps. Thus, for the controlled current charger to be effective, support circuitry was needed to sense and integrate the current supplied to the defibrillator (as opposed to the current supplied to the battery) by the charger so that the charger could maintain a measure of the current supplied to the battery.

SUMMARY OF THE INVENTION

The invention provides a detachable power supply that can be quickly and securely attached to a portable defibrillator so that the power supply and the defibrillator form an integral unit. This ease of attachment is vital in the emergency situations in which portable defibrillators are typically employed. In addition, because the power supply can be securely attached to the defibrillator, and because the power supply is both compact and lightweight, use of the power supply does not significantly reduce from the portability of the defibrillator.

Though compact and lightweight, the detachable power supply offers the advantages of both controlled current and controlled voltage power supplies. When the defibrillator is turned on, the power supply operates in a controlled voltage mode, and thereby ensures that the defibrillator is powered by a predictable, generally constant, controlled input voltage. However, when the defibrillator is turned off, and the battery needs to be charged, the power supply operates in a controlled current mode. Use of the controlled current mode allows for quick charging of the battery, and thereby maximizes the likelihood that the battery will be in a fully charged state when a source of AC power is unavailable.

In one aspect, generally, the invention features a detachable power supply for supplying power from an external power source to a portable defibrillator for charging a battery of the portable defibrillator and operating the portable defibrillator. The power supply includes a housing shaped to attach to the defibrillator, and a latch connected to the housing for mechanically attaching the power supply to the defibrillator so that the power supply and the defibrillator form a portable, integral unit. Typically, the height and width of the housing are dimensioned so that the housing conforms to the dimensions of the portable defibrillator. Such dimensioning eases handling and storage of the defibrillator when the power supply is attached, and thereby prevents the power supply from negatively impacting the portability of the defibrillator.

The power supply also includes an electrical connector connected to the housing to supply power to the defibrillator. The connector is located so that it engages a mating electrical connector on the defibrillator as the latch is engaged to connect the power supply to the defibrillator. Use of such a connector, as opposed to, for example, a cord, dramatically simplifies connection of the power supply to the defibrillator, and ensures that, when the power supply is physically attached to both the defibrillator and the external power source, the power supply will be able to supply power to the defibrillator.

Finally, the power supply includes an external power connection, typically a cord, for bringing external power into the power supply and a power module installed within the housing and having a power circuit that converts power from the external power source to a form useable by the portable defibrillator. The output of the power module is connected to the electrical connector to deliver power to the defibrillator.

To allow quick connection of the power supply to the defibrillator, the latch can include a mechanism for attaching the power supply to the defibrillator without manipulating the latch. The power supply can also include an elongated hook member for insertion into a slot located in a housing of the defibrillator. In this case, the hook member, in combination with the latch, secures the power supply to the defibrillator. Typically, the hook member is located near the top of the power supply and the latch is located near the bottom of the power supply.

To allow quick detachment of the power supply from the defibrillator, the power supply can also include a latch release that, when pressed, enables detachment of the power supply from the defibrillator. This latch release can be lockable to prevent detachment of the power supply from the portable defibrillator.

For safety purposes, the power supply can include an interlock switch that connects the electrical connector to the power module when the power supply is attached to the portable defibrillator, and isolates the electrical connector from the power module when the power supply is detached from the portable defibrillator. This ensures that the electrical connector will never be powered when the power supply is not connected to the defibrillator, and thereby eliminates any risk that a person handling the power supply would be shocked by the power supply.

To enhance portability, the housing of the power supply can include a recess for storage of the cord. Typically, the recess is a depression extending around the full circumference of a portion of the housing. The depression is sized so that the cord may be wrapped around the housing and be substantially fully contained within the depression. The housing can also include a separate recess for storage of a plug of the cord.

To provide optimal charging and operational performance, the power module of the power supply can be alternately operable in both a controlled current mode and a controlled voltage mode. Typically, the power module operates in the controlled voltage mode when the defibrillator is turned on. The power module typically operates in the controlled current mode only when the defibrillator is turned off and a current supplied to the defibrillator when the power supply operates in the controlled voltage mode is less than or equal to a predetermined value.

In another aspect, generally, the invention features a controlled current/controlled voltage power supply for supplying power from an external power source to a portable defibrillator for charging a battery of the defibrillator and operating the defibrillator. The power supply includes an external power connection for bringing external power into the power supply, a power module, and a controller. The power module has a power circuit that converts power from the external power source to a form useable by the portable defibrillator, is alternately operable in either a controlled current mode or a controlled voltage mode, and has an output connected to deliver power to the defibrillator. The controller switches the power module between the controlled current mode and the controlled voltage mode.

This dual-mode power supply provides rapid battery charging which, as noted above, is of particular significance when the defibrillator employs lead acid or other types of batteries that tend to lose their ability to retain charge when put into service before being fully charged. Because this power supply rapidly charges the battery, it reduces the likelihood that the battery will be put into service before being fully charged. In addition, because this power supply operates in a controlled voltage made suitable for directly powering the defibrillator, it further reduces the likelihood that a partially charged battery will need to supply power to the defibrillator.

Other features and advantages of the invention will be apparent from the following description of the preferred embodiments and from the claims.

DESCRIPTION OF THE PREFERRED EMBODIMENTS

Figure 1:
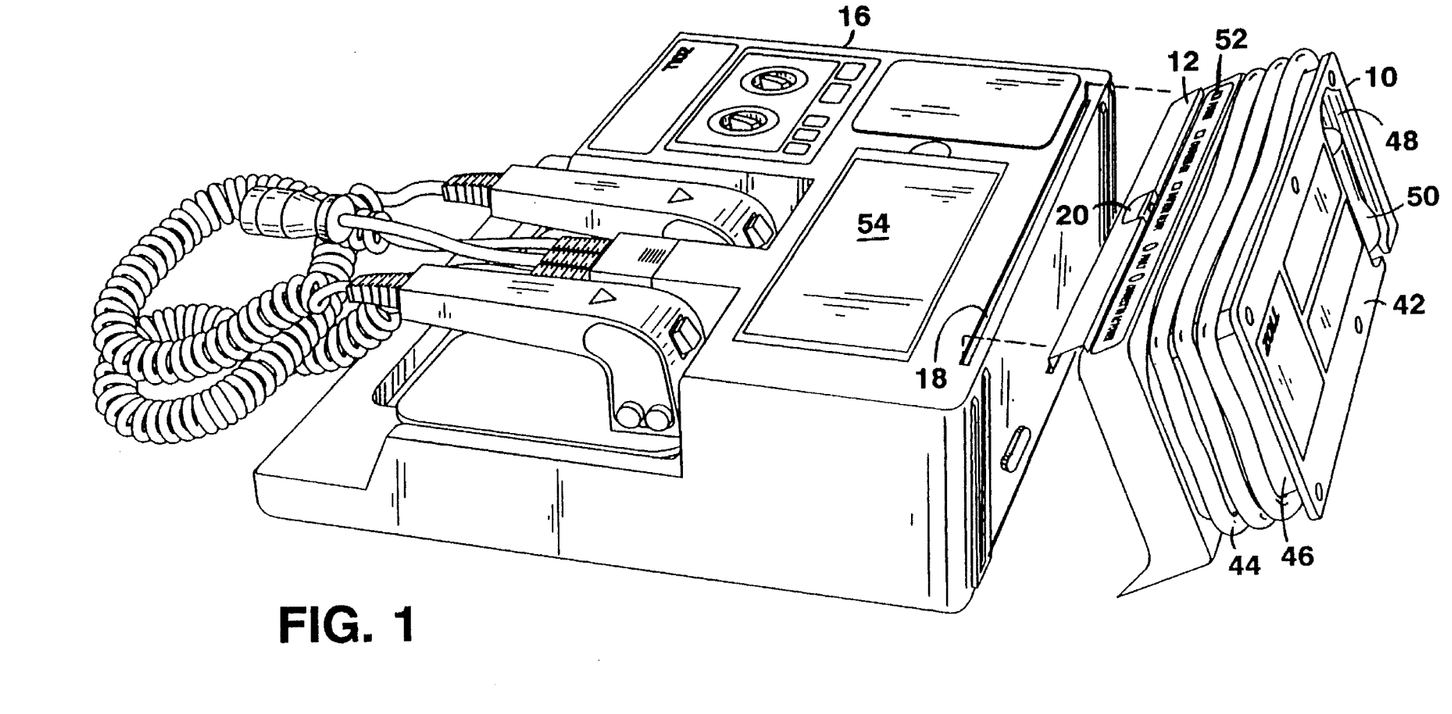
FIG. 1 is a perspective view of a detachable power supply and a portable defibrillator.
Figure 2:
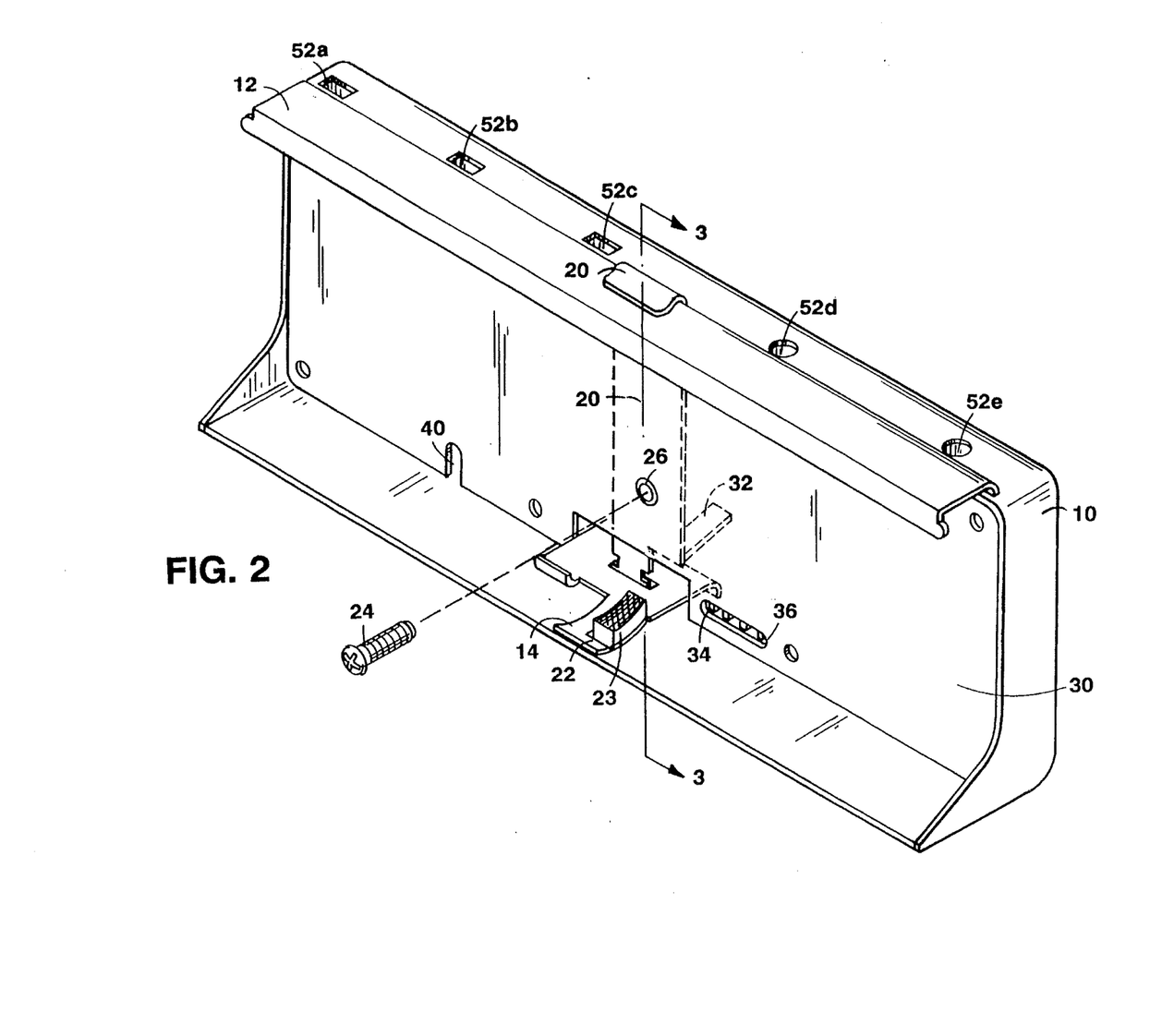
FIG. 2 is a perspective view of the power supply of FIG. 1.

FIGS. 1 and 2 show a portable defibrillator 16 and detachable power supply 10. The detachable power supply 10 includes a continuous and elongated hook member 12 located near the top of the power supply and a latch 14 (see FIG. 2) located near the bottom of the power supply for attachment to the portable defibrillator 16. Power supply 10 is attached by placing hook member 12 in a slot 18 in the upper housing of the defibrillator and engaging the latch. The power supply is detached by pressing a latch release 20 to disengage the latch.

Specifically, the top of the power supply is held in place against the defibrillator by the engagement of hook member 12 with slot 18. The power supply is swung into place so that a portion 22 of latch 14 secures the bottom of the power supply to a portion 23 of the lower housing of the defibrillator. The power supply is released by pressing on latch release 20, which protrudes through the top edge of the power supply. Thus, the power supply can be attached to and released from the defibrillator with a single hand, and without manipulating the latch.

Latch 14 is a piece of stamped sheet metal which, when attached, links the housing of the power supply to the housing of the defibrillator. The latch, which can be disengaged only when unstressed, is designed so that increased pull on the housings to separate them makes the latch harder to disengage.

Figure 3:
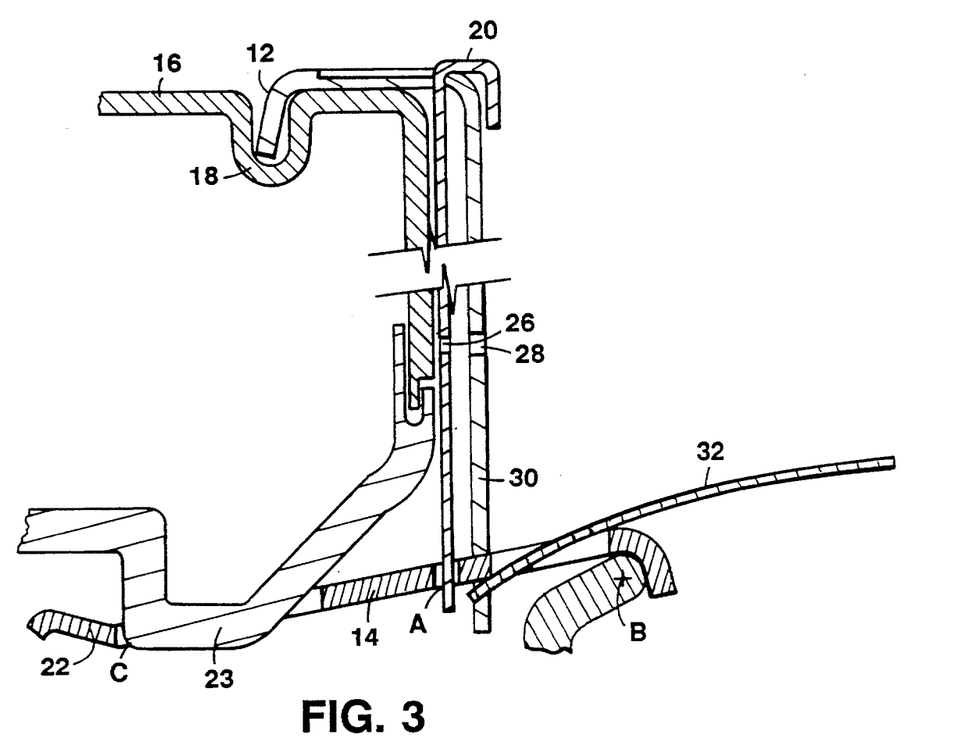
FIG. 3 is a cutaway side view of the power supply of FIG. 2 taken along line 3—3 of FIG. 2.

Referring also to FIG. 3, latch 14 is locked by putting a screw 24 (FIG. 2) through a hole 26 in latch release 20 and into a threaded insert 28 in a metal cover plate 30 of the power supply. When screw 24 is in place, the position of the latch release is fixed, and the latch pivots around its engagement with the latch release at point A. In this configuration, the power supply can still be attached to the defibrillator, but cannot be detached without using a tool. The latch is disengaged, and the power supply is detached, by taking a tool (e.g., a screwdriver) and pushing on the back edge of the latch (near point B) so that the latch disengages at point C. (The power supply cannot be detached by removing screw 24 because, when the power supply is attached to the defibrillator, screw 24 is located between the power supply and the defibrillator.)

When screw 24 is not in place, latch release 20 is free to move up and down, and the latch pivots around its engagement at point B with the housing of power supply 10. The latch release is biased upward by pressure exerted on the latch by a spring 32 located within the power supply. When the latch release is pressed downward, pivoting of the latch about point B causes the latch to disengage at point C. Once the latch is disengaged, the power supply is removed by swinging the bottom of the power supply away from the defibrillator, and removing the hook member from the slot.

Power supply 10 makes electrical connection with portable defibrillator 16 through pins 34a–34e (see FIG. 4), referred to collectively as pins 34, located within a port 36. Pins 34 fit within a socket 38 on the defibrillator. For safety reasons, power pin 34a is only active when the power supply is attached to the defibrillator. When the power supply is attached to the defibrillator, an extension (not shown) on the defibrillator closes two series interlock switches 39 (see FIG. 4) located within a recess 40 on the power supply, and thereby activates power pin 34a. Interlock switches 39 isolate power pin 34a from a power module 58 (see FIG. 4) of the power supply when the power supply is detached from the defibrillator.

Power supply 10 also includes a ruggedized base 42 and an eight-foot, integral cord 44. For storage of integral cord 44, base 42 includes an indentation 46 around its periphery and a recess 48 at its back end. Indentation 46 and recess 48 are configured so that integral cord 44 can be wrapped around indentation 46 and a plug 50 of integral cord 44 can be secured in recess 48. Recess 48 is configured so that plug 50 is flush with the surface of base 42 when stored within recess 48, which allows the defibrillator to stand on end even when the power supply is attached and plug 50 is secured in recess 48.

Another external feature of the power supply is a set of five indicator LEDs (light emitting diodes) 52a–52e, referred to collectively as indicator LEDs 52, located along the top of the power supply. Yellow indicator LED 52a is lit when the power supply is connected to a source of AC power and capable of operating the defibrillator and/or charging a battery 54 of the defibrillator. Yellow indicator LED 52b is lit when battery 54 is installed in the defibrillator and is receiving a charge. Green indicator LED 52c is lit when battery 54 is fully charged and therefore ready for use. Yellow indicator LED 52d is lit when a fault is detected in the power supply or battery 54. Finally, flashing yellow indicator LED 52e is activated when the power supply needs to be connected to a source of AC power, which occurs when the power supply is attached to the defibrillator and not connected to a source of AC power, battery 54 is in place, and the defibrillator is turned off. An audible signal is also produced by a beeper 56 (see FIG. 4). Beeper 56 is programmable so that the audible signal is sounded only upon expiration of a predetermined delay period (e.g., after the power supply has needed to be, and has not been, connected to a source of AC power for thirty minutes).

The power supply is 10.5 inches (26.7 cm) wide, 4 inches (10.2 cm) high, and 2.5 inches (6.4 cm) deep, and weighs 3.1 pounds (1.4 kg). While the housing of the power supply is made typically from a molded polymer, other materials such as, for example, coated magnesium could also be used. The power supply is configurable to operate with AC input voltages of 90–135 (110) or 190–265 (220) volts at frequencies of 50 or 60 Hz, and also works with a 165 volt square wave converter, such as is commonly available in ambulances. The power supply powers the defibrillator regardless of whether a battery is present in the defibrillator.

Figure 4:
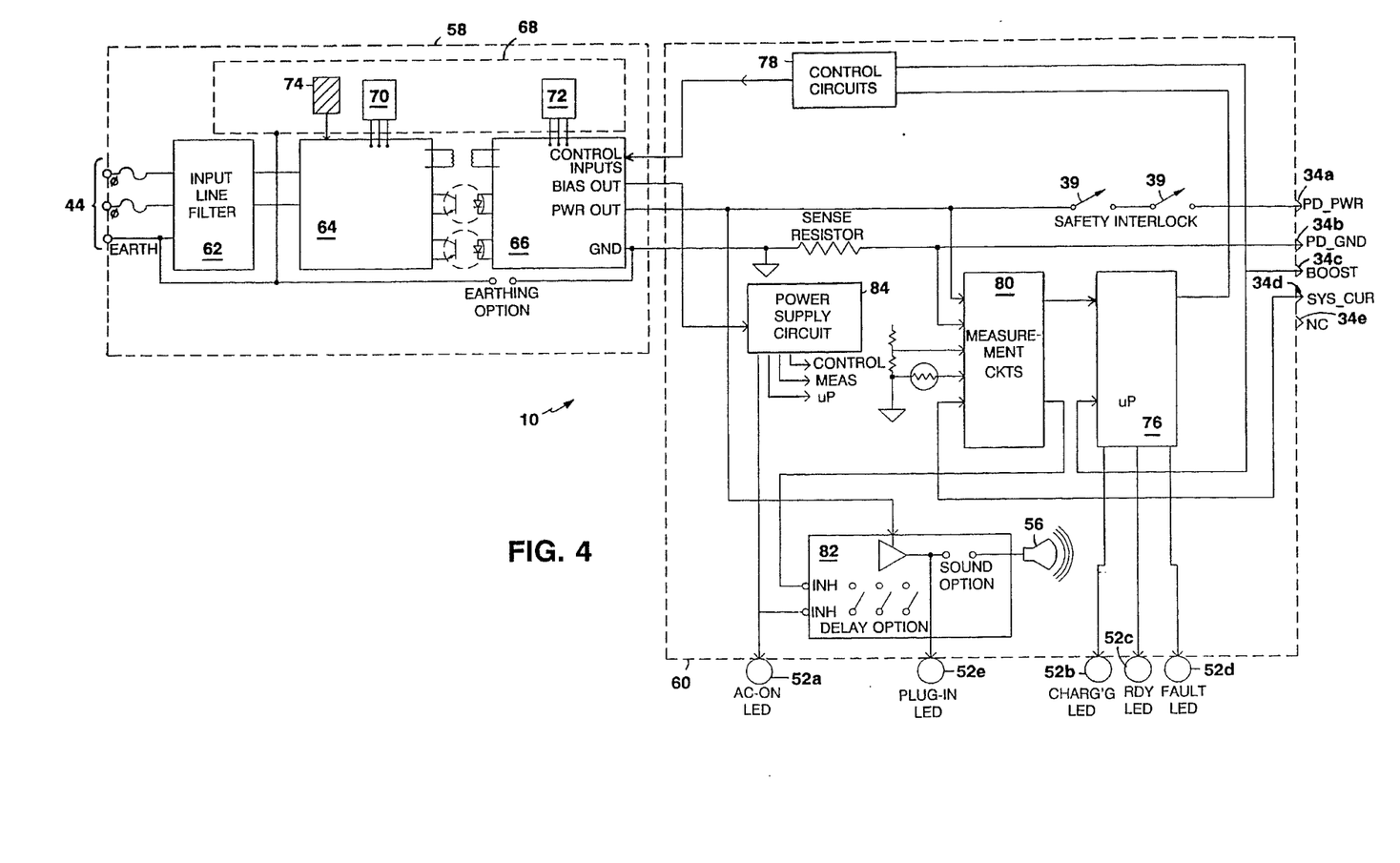
FIG. 4 is a block diagram of the power supply of FIG. 2.

Referring to FIG. 4, power supply 10 includes a power module 58 and a control module 60. Power module 58 includes an input line filter 62 that is connected to integral cord 44 and shapes the input voltage therefrom, a voltage selector 64 that allows configurable selection between input voltages of 110 volts and 220 volts, and an output circuit 66 that, in response to control inputs, produces either a controlled voltage or a controlled current. Power module 58 also includes a heat sink 68 connected to heat producing components 70, 72 of, respectively voltage selector 64 and output circuit 66. A thermal shutdown device 74 that shuts down power module 58 in response to excessive heat is also connected to heat sink 68.

Output circuit 66 operates in either a controlled voltage charging mode, in which it delivers a generally constant output voltage of about 11.75 volts at up to 3.5 amps; a low voltage charging mode, in which it delivers a generally constant output voltage of about 10.75 volts at up to 10.0 amps; a controlled current charging mode, in which it delivers a generally constant output current of up to 0.835 amps at a voltage of up to 16.5 volts, and a battery search mode, in which it delivers a generally constant output voltage of 15 volts at up to 0.3 amps. Though the controlled voltages or currents are generally constant, some variation is allowed. For example, in the preferred embodiment, the 11.75 volt output voltage in the controlled voltage charging mode can vary between 11.5 and 12 volts, while the 10.75 volt output voltage in the low voltage charging mode can vary between 10.3 and 10.9 volts. Similarly, the output current in the controlled current charging mode can vary between 0.735 and 0.935 amps.

Figure 5:
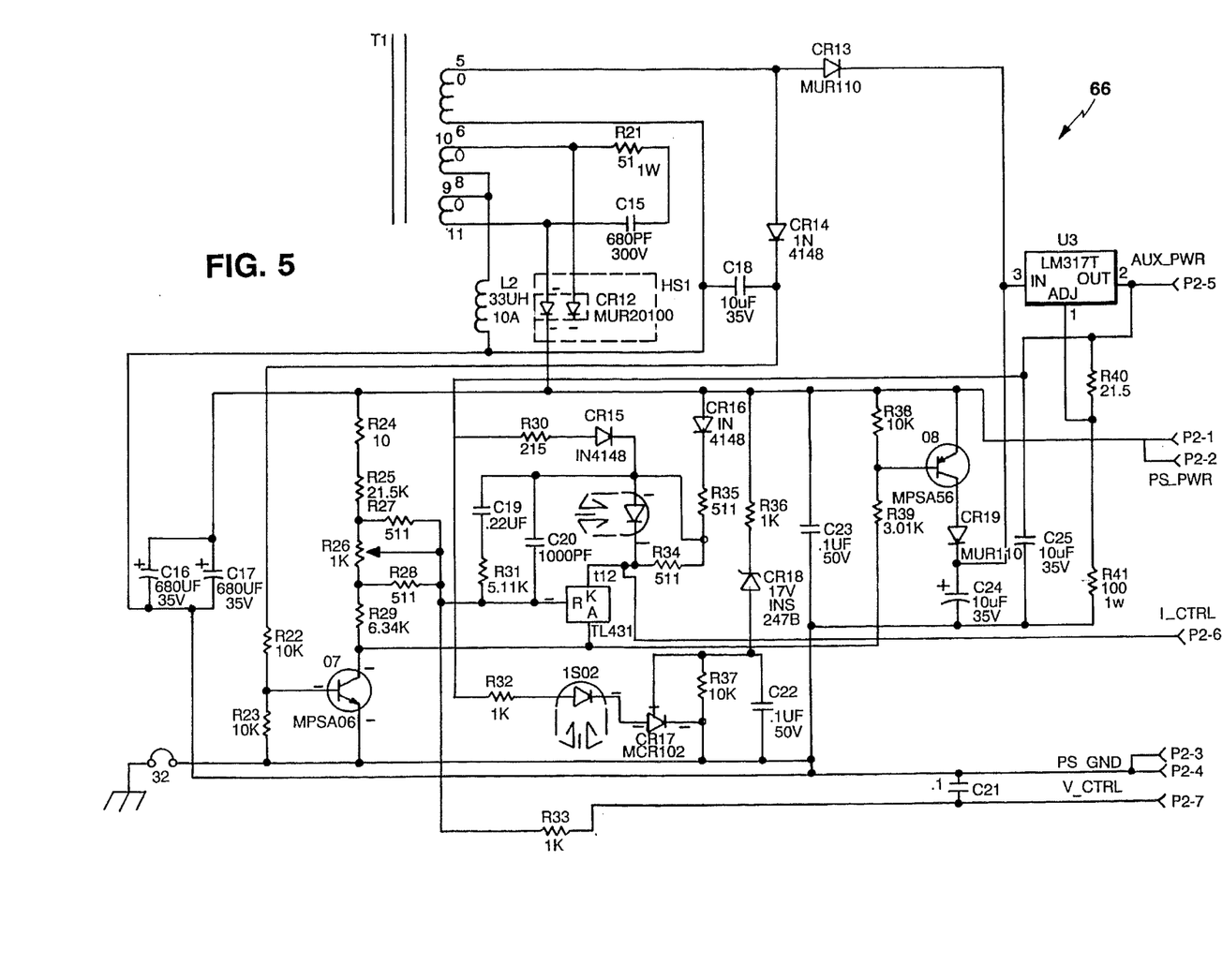
FIG. 5 is a circuit diagram of an output circuit of a power module of the power supply of FIG. 2.

Referring to FIG. 5, output circuit 66 rectifies the alternating voltage and current from the transformer secondary (T1) through the two legs of a center tap 100 V Schottky diode (CR12). During the dead time between power cycles, both diode legs are forward biased and the magnetizing current in the transformer appears as an offset between the two currents. Leakage spikes from the transformer are snubbed to a safe reverse voltage level by R21 and C15.

The rectified transformer voltage appears across an output filter that includes a 33 µH inductor (L2) and two 680 µF capacitors (C16 and C17). During power transfer, the rectified transformer voltage energizes the inductor and provides output current to the load. During dead time, the inductor provides the energy delivered to the load. The inductor current is continuously flowing for normal operating loads greater than 1.6 A.

The output voltage (PS_PWR) of output circuit 66 is sensed by a set of resistors (R24 through R29) that includes a potentiometer (R26) for factory adjustment. A tap off these resistors, which has a nominal value of 2.5 volts, connects to a reference pin (R) of a band gap device (U2). This connection functions as the negative input of an error amplifier of a feedback control loop. This loop is stabilized by compensation provided by C19, C20, and R31.

The output voltage of output circuit 66 is regulated to hold the reference pin of the band gap device (U2) sufficiently above 2.5 V to cause the cathode (K) of the band gap device to sink a required current through the diode of the optocoupler IS01. The current required through the optocoupler diode is determined by the current required through the transistor of IS01 (which is located in voltage selector 64). The current through the transistor of IS01 sets the duty cycle of the output of voltage selector 64 to a value that allows output circuit 66 to produce a desired output voltage. Bias current for the optocoupler diode is provided from the output of output circuit 66 through R30 and CR15, and from the auxiliary output (AUX_PWR) of output circuit 66 through R35 and CR16. Bias current is redundantly supplied by the auxiliary output for fault condition operation. In normal operation, the auxiliary output is set between 6.5 volts and 7.5 volts, and diode CR16 is back-biased so that noise from the auxiliary output is not coupled into the control circuit.

The control circuitry connected to the output of output circuit 66 draws approximately 12 mA. Because the product application requires the output to be connected directly across a battery, the battery would be drained by this control circuitry if line power were not provided to output circuit 66. To avoid draining the battery, the control circuitry is switched on and off through an NPN transistor (Q7). Current to turn on this transistor is provided from a tap winding off of the transformer and a resistor network (R22 and R23).

Output circuit 66 is set so that its output voltage (PS_PWR) does not exceed 17.6 volts. If the voltage exceeds this level, an over voltage protection circuit is activated. This circuit includes a 17 volt zener diode (CR18) that, when the output voltage exceeds 17.6 volts, conducts enough to drive the gate of an SCR (CR17) above threshold. When the gate of the SCR is driven above threshold, current is driven through the diode of optocoupler IS02 through R32 from the auxiliary output. Current flowing through the diode of optocoupler IS02 inhibits the production of power by voltage selector 64 until the output voltage drops to the point where the IS02 diode no longer conducts. At that point, voltage selector 64 is again able to produce power.

The auxiliary output (AUX_PWR) is set by an LM317T adjustable three terminal regulator (U3). In normal operation, input power to this device is provided by a tap off of the transformer. However, the auxiliary must be kept turned on during transitions for which the power supply is back driven by a battery. In those cases, auxiliary power is provided from the battery through Q8 and CR19. Q8 has a particular functional window within which it is operational. When the power supply is not providing any power, Q7 is off, which turns Q8 off and ensures that the battery is not drained. When the power supply is providing normal operating power, CR19 is back biased by the tap winding.

Output circuit 66 interfaces with control module 60 through an eight conductor cable harness terminated on each end with an eight position crimp terminal housing which mates with a PCB mounted connector. The pin assignment at the interface is as follows:

| Pin Number | Function | Title |
| --- | --- | --- |
| 1 | Output (+) | PS_PWR |
| 2 | Output (+) | PS_PWR |
| 3 | Output (−) | PS_GND |
| 4 | Output (−) | PS_GND |
| 5 | Auxiliary (+) | AUX_PWR |
| 6 | Current Control | I_CTRL |
| 7 | Voltage Control | V_CTRL |
| 8 | No Connection | N/A |

Two conductors each are provided for both the output power and output ground to minimize voltage drops under heavy load. The output is regulated on the power supply and therefore does not compensate for drops through the connector.

The output voltage is nominally set to 10.75 volts. When required by the system, the voltage setting is changed by connecting the voltage control line (V_CTRL) to a fixed voltage (5 volts or 0 volts) through one of a set of fixed resistances in control module 60. This control signal changes the voltage/impedance characteristics of the reference pin of U2. Through the possible control signals, control module 60 can set the voltage within a range of 10.75 volts to 16.25 volts. The control line is protected from electro static discharge with a series, one kiloohm resistor (R33).

The output current is sensed by control module 60. This current sense signal is used to provide over current protection and current control as required by the system. The control signal to the power supply is in the form of a sink current through the diode of optocoupler IS01. When active, this control signal overrides the voltage control because the cathode (K) of U2 enters an open circuit mode when the output voltage causes the U2 reference voltage to fall below 2.5 V.

To provide over current protection while the output collapses, the diode of IS01 receives current from the auxiliary output in addition to the main output. Control module 60 thus can drive the main output down to zero volts in severe over current conditions.

Referring again to FIG. 4, control module 60 includes a microprocessor 76 that has overall control of the power supply. Microprocessor 76 is an 87C752 processor running at 6.144 MHz with two kilobytes of internal ROM and 64 bytes of internal RAM. Microprocessor 76 includes a six bit I/O port and two eight bit I/O ports.

A control circuit 78 responds to signals from microprocessor 76 and a BOOST signal from the defibrillator to supply control signals to output circuit 66. The defibrillator turns on the BOOST signal when the defibrillator is producing a pace pulse or otherwise needs to receive defibrillation charge energy. In control module 60, the BOOST signal, which is received on pin 34c, is input into a comparator that produces a digital (high/low) output. This digital output is supplied to microprocessor 76 for control of the power supply and, in particular, output circuit 66. In addition, to ensure that the power supply immediately responds to the BOOST signal, the digital output is supplied directly to control circuit 78.

Measurement circuits 80 monitor the output voltage of output circuit 66, the current supplied to battery 54, and other signals, to provide information that allows microprocessor 76 to determine the charge status of battery 54.

Other components of control module 60 include beeper/LED drive circuitry 82 that activates LED 52e and beeper 56 under the conditions described above, and a power supply circuit 84 that supplies operating power to microprocessor 76, control circuits 78, measurement circuits 80, and beeper/LED drive circuitry 82. Power supply circuit 84 is powered by the auxiliary output (AUX_PWR) of output circuit 66.

Generally, microprocessor 76 configures the power supply to deliver a controlled voltage when the defibrillator is turned on, and either a controlled voltage or a controlled current when the defibrillator is turned off. Use of a controlled current reduces the time required to charge a battery of the defibrillator from about sixteen hours to about three hours.

Figure 6:
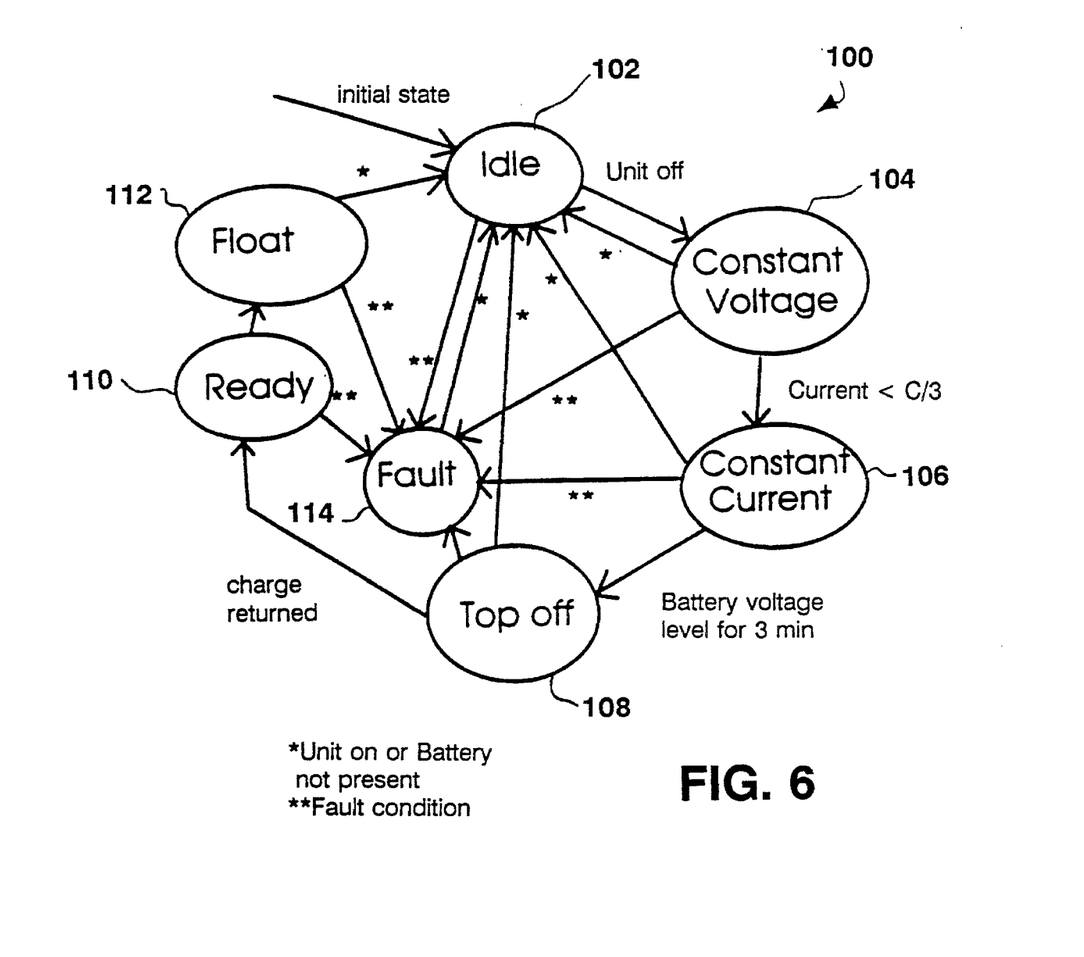
FIG. 6 is a state diagram for a charging procedure implemented by the power supply of FIG. 2.

More specifically, as illustrated in FIG. 6, microprocessor 76 controls delivery of power according to a procedure 100 that microprocessor 76 invokes approximately once every 10 milliseconds. In implementing procedure 100, processor 76 monitors several characteristics of the power supply and the defibrillator, including the voltage level of battery 54, the current supplied to the defibrillator, the on/off state of the defibrillator, and the presence or absence of battery 54 and/or the BOOST signal from the defibrillator. Microprocessor 76 determines the on/off state of the defibrillator from a signal received on pin 34d.

At initialization, the power supply operates in an IDLE state 102. In IDLE state 102, output circuit 66 operates in low voltage mode if the power supply is connected to the defibrillator and the BOOST signal from the defibrillator is on, and otherwise operates in controlled voltage mode.

The power supply transitions from IDLE state 102 to a CONSTANT VOLTAGE state 104 when the power supply is connected to the defibrillator, the defibrillator is turned off, battery 54 is present, and the BOOST signal is off. In making the transition, microprocessor 76 resets an integrated total charge value.

In IDLE state 102, if portable defibrillator is turned off, microprocessor 76 determines whether battery 54 is present by implementing a battery search procedure. First, microprocessor 76 places output circuit 66 in battery search mode. After waiting for 50 milliseconds to allow the output voltage to reflect the change in the charging mode, microprocessor 76 measures the current being delivered to the defibrillator. If this current exceeds 100 milliamps, the microprocessor 76 determines that battery 54 is present. Otherwise, microprocessor 76 determines that battery 54 is not present. Thereafter, microprocessor 76 places output circuit 76 in controlled voltage mode and waits for 50 milliseconds to allow the output voltage to reflect the change in the charging mode. Typically, microprocessor 76 activates the battery search mode once every 500 milliseconds.

In CONSTANT VOLTAGE state 104, output circuit 66 operates in the controlled voltage mode. During charging, microprocessor 76 periodically adds a measure of the current being supplied to the defibrillator to the integrated total charge value, and thereby maintains a measure of the total charge being supplied to battery 54.

The power supply transitions from CONSTANT VOLTAGE state 104 to a CONSTANT CURRENT state 106 when the average current supplied to the defibrillator is less than or equal to a predetermined controlled current charging rate. The power supply returns to IDLE state 102 from CONSTANT VOLTAGE state 104 when the power supply is disconnected from the defibrillator or the defibrillator is turned on. (If battery 54 is not present, this will cause the current to fall below the controlled current charging rate.)

In CONSTANT CURRENT state 106, output circuit 66 operates in the controlled current mode and supplies current at the controlled current charging rate. Microprocessor 76 continues to periodically add the current being supplied to the defibrillator to the integrated total charge value. The power supply transitions from CONSTANT CURRENT state 106 to a TOP OFF state 108 when the average battery voltage remains level for three minutes, or begins to drop. The power supply transitions from CONSTANT CURRENT state 106 to IDLE state 102 when the power supply is disconnected from the defibrillator, the defibrillator is turned on, or battery 54 is not present. In CONSTANT CURRENT state 106, microprocessor 76 determines that battery 54 is not present if the measured battery voltage exceeds 15.5 volts.

In TOP OFF state 108, output circuit 66 continues to operate in the controlled current mode and supplies current at the controlled current charging rate. The power supply transitions from TOP OFF state 108 to a READY state 110 when a time period equal to the integrated total charge value divided by sixteen elapses. The power supply transitions from TOP OFF state 108 to IDLE state 102 when the power supply is disconnected from the defibrillator or the defibrillator is turned on.

In READY state 110, output circuit 66 operates in the controlled voltage mode, and microprocessor 76 activates LED 52c to indicate that battery 54 is fully charged. After LED 52c is activated, the power supply transitions to a FLOAT state 112.

In FLOAT state 112, output circuit 66 operates in the controlled voltage mode. The power supply transitions from FLOAT state 112 to IDLE state 102 when the power supply is disconnected from the defibrillator, the defibrillator is turned on, or battery 54 is not present. As in IDLE state 102, microprocessor 76 determines whether battery 54 is present by switching output circuit 76 to the battery search mode.

Finally, if at any time during charging microprocessor 76 detects a fault in the power supply, microprocessor 76 causes the power supply to transition to a FAULT state 114. In FAULT state 114, output circuit operates in low voltage mode if the BOOST signal is on, and otherwise operates in controlled voltage mode. To indicate the presence of a fault, microprocessor 76 turns on LED 52d and, if LED 52c is on, turns off LED 52c (microprocessor 76 also turns off LED 52c in IDLE state 102). The power supply remains in FAULT state 114 until the fault is corrected, at which point the power supply transitions to IDLE state 102.

Other embodiments are within the following claims.

What is claimed is:

1. A detachable power supply for supplying power from an external power source to a portable defibrillator for charging a battery of the portable defibrillator and operating the portable defibrillator, comprising:

a housing shaped to attach to the portable defibrillator;

a latch connected to the housing for mechanically attaching the detachable power supply to the portable defibrillator so that the detachable power supply and the portable defibrillator form a portable, integral unit;

an electrical connector connected to the housing, the connector supplying power from the power supply to the portable defibrillator, the connector being located so that it engages a mating electrical connector on the portable defibrillator as the latch is engaged to connect the power supply to the defibrillator;

an external power connection for bringing power from outside of the housing of the power supply into the housing of the power supply;

a power module installed within the housing, the power module having a power circuit that is operable to convert power from the external power source to a form useable by the portable defibrillator, the output of the power module being connected to the electrical connector to deliver power to the portable defibrillator in the form useable by the portable defibrillator.

2. The detachable power supply of claim 1 wherein the height and width of the housing are dimensioned so that the housing conforms to dimensions of the portable defibrillator.

3. The detachable power supply of claim 1 wherein the latch includes a mechanism operable to attach the power supply to the portable defibrillator without manipulating the latch.

4. The detachable power supply of claim 3 further comprising an elongated hook member for insertion into a slot located in a housing of the portable defibrillator, wherein the hook member, in combination with the latch, secures the power supply to the portable defibrillator.

5. The detachable power supply of claim 4 wherein the power supply has a top and a bottom and wherein the hook member is located near the top of the power supply and the latch is located near the bottom of the power supply.

6. The detachable power supply of claim 1 further comprising a latch release that, when pressed, is operable to enable detachment of the power supply from the portable defibrillator.

7. The detachable power supply of claim 6 wherein the latch release is operable to be locked to prevent detachment of the power supply from the portable defibrillator.

8. The detachable power supply of claim 1 further comprising an interlock switch connected between the electrical connector and the power module and operable to electrically connect the electrical connector to the power module when the power supply is attached to the portable defibrillator, and electrically isolate the electrical connector from the power module when the power supply is detached from the portable defibrillator.

9. The detachable power supply of claim 1 wherein the external power connection is a cord.

10. The detachable power supply of claim 9 wherein the housing includes a recess for storage of the cord.

11. The detachable power supply of claim 10 wherein the recess is a depression extending around a full circumference of the housing, the depression being sized so that the cord may be wrapped around the housing and be substantially fully contained within the depression.

12. The detachable power supply of claim 10 wherein the cord includes a plug and the housing includes a separate recess for storage of the plug.

13. The detachable power supply of claim 1 wherein the power module is operable in both a controlled current mode and a controlled voltage mode and wherein the power module includes circuitry operable to switch operation of the power module between the controlled current mode and the controlled voltage mode.

14. The detachable power supply of claim 13 wherein the power supply includes means for operating the power module in the controlled voltage mode when the portable defibrillator is turned on.

15. The detachable power supply of claim 14 wherein the power supply includes means for operating the power module in the controlled current mode when the portable defibrillator is turned off.

16. The detachable power supply of claim 15 wherein the power supply includes means for operating the power module in the controlled current mode only when the portable defibrillator is turned off and a current supplied to the portable defibrillator when the power supply operates in the controlled voltage mode is less than or equal to a predetermined value.

17. A power supply for supplying power from an external power source to a portable defibrillator for charging a battery of the portable defibrillator and operating the portable defibrillator, comprising:

an external power connection for bringing external power into the power supply;

a power module having a power circuit that converts power from the external power source to a form useable by the portable defibrillator, the power module being operable in a controlled current mode and a controlled voltage mode, and the output of the power module being connected to deliver power to the defibrillator; and a controller operable to control whether the power module operates in the controlled voltage mode or the controlled current mode.

18. The power supply of claim 17 wherein the controller is operable to control the power module to operate in the controlled voltage mode when the portable defibrillator is turned on.

19. The power supply of claim 18 wherein the controller is operable to control the power module to operate in the controlled current mode when the portable defibrillator is turned off.

20. The power supply of claim 19 wherein the controller is operable to control the power module to operate in the controlled current mode only when the portable defibrillator is turned off.

21. The power supply of claim 20 wherein the controller is operable to control the power module to operate in the controlled current mode only when the portable defibrillator is turned off and a current supplied to the portable defibrillator when the power supply operates in the controlled voltage mode is less than or equal to a predetermined value.

22. The power supply of claim 21 wherein the controller is operable to monitor characteristics of the power supply and the defibrillator, and to control the power module to operate in either the controlled voltage mode or the controlled current mode in response to the monitored characteristics.

23. The power supply of claim 22 wherein the controller is operable to monitor for the presence or absence of a battery in the defibrillator.

24. The power supply of claim 23 wherein the controller is operable to determine the presence or absence of a battery in the defibrillator by monitoring current delivered to the defibrillator.

25. The power supply of claim 24 wherein the controller is operable to determine that a battery is present when the current delivered to the defibrillator exceeds a predetermined value.

26. The power supply of claim 17 wherein the controller is operable to monitor characteristics of the power supply and the defibrillator, and to control the power module to operate inn either the controlled voltage mode or the controlled current mode in response to the monitored characteristics.

27. The power supply of claim 26 wherein the power module is also operable in a low voltage mode, and wherein the controller is operable to control the power module to operate in the low voltage mode in response to a signal from the defibrillator that the defibrillator needs charging energy.

28. The power supply of claim 26 wherein the controller is operable to switch operation of the power module from the controlled voltage mode to the controlled current mode when the voltage across the battery is level or decreasing for a predetermined time period.

29. The power supply of claim 28 wherein the controller is operable to wait for a delay period before switching operation of the power module to the controlled voltage mode.

30. The power supply of claim 29 wherein the delay period is related to the total charge supplied to the battery.

31. The power supply of claim 26 wherein the controller is operable to monitor for the presence or absence of a battery in the defibrillator.

32. The power supply of claim 31 wherein the controller is operable to determine the presence or absence of a battery in the defibrillator by monitoring current delivered to the defibrillator.

33. The power supply of claim 32 wherein the controller is operable to determine that a battery is present when the current delivered to the defibrillator exceeds a predetermined value.

34. The power supply of claim 33 further comprising a housing and an electrical connector connected to the housing, the connector being connected to the output of the power module and being operable to supply power from the power supply to the portable defibrillator, wherein the power module is installed within the housing.

* * * * *